United States Patent [19]

Maldarelli et al.

[11] 4,140,018
[45] Feb. 20, 1979

[54] PROGRAMMABLE ACTION SAMPLER SYSTEM

[75] Inventors: Lawrence V. Maldarelli, Tustin; David T. Phillips; William L. Proctor, both of Goleta; Philip J. Wyatt, Santa Barbara; Thomas C. Urquhart, Carpinteria, all of Calif.

[73] Assignee: Science Spectrum, Inc., Santa Barbara, Calif.

[21] Appl. No.: 831,293

[22] Filed: Sep. 7, 1977

[51] Int. Cl.² ............................................. G01N 1/14
[52] U.S. Cl. ................................................. 73/423 A
[58] Field of Search ...................... 73/423 A, 425.6; 141/130

[56] References Cited

U.S. PATENT DOCUMENTS

| | | | |
|---|---|---|---|
| 2,604,249 | 9/1952 | Gorham | 141/130 |
| 3,143,393 | 8/1964 | Des Hons | 73/425.6 |
| 3,168,124 | 2/1965 | Lenkey | 141/130 |
| 3,542,093 | 11/1970 | Pollmann | 141/130 |
| 3,811,780 | 5/1974 | Liston | 73/423 A |
| 3,911,749 | 10/1975 | Hendry | 73/423 A |
| 4,041,763 | 8/1977 | Pfleger | 73/423 A |

*Primary Examiner*—S. Clement Swisher
*Attorney, Agent, or Firm*—Spensley, Horn & Lubitz

[57] ABSTRACT

A programmable action sampler system (PASS) is described which holds a large number of discrete samples in a matrix of separate sample cups. The system is capable of dispensing a sample from a sample line into any one of the sample cups. At a pre-determined later time, using a cannula, the system addresses the sample from the cup for further measurement or analysis. In the preferred system, the samples flow sequentially through a tube, the liquid intermediate the samples being dispensed into a liquid waste line. The cannula between samples is bathed constantly in a wash tube, even while moving from one sample location to another. Further, in the preferred application, bacterial samples are employed, the sample cups being immersed in a constant temperature liquid bath to hold the bacterial samples at a constant incubation temperature. Among the various novel features employed in the system is a blade brake structure that accurately locates the sample head and cannula over any selected sample cup.

18 Claims, 15 Drawing Figures

PROGRAMMABLE ACTION SAMPLER SYSTEM

INTRODUCTION

The invention concerns a programmable action sampler system (PASS) preferably one which both rapidly and accurately either dispenses a sample into one of numerous sample positions or addresses a sample in one of such numerous positions for analysis or further processing, the positions being randomly addressable.

In many applications, it is necessary to store a large number of discrete samples under pre-determined conditions for various times. For example, when handling bacterial samples, it may be necessary to incubate such samples in a constant temperature environment for many hours or even days at a time. As another example, during chemical reactions, it may be necessary to store the reacting samples in a controlled environment for extended periods and to, during such periods, repetitively measure the state of the reaction. There are automated systems capable of storing samples for extended periods. However, such systems require the samples to be sequentially addressed, and often prevent measurement of the samples at other than pre-determined sequential times. Thus, such systems are highly limited in their capability and, even though expensive, lack the versatility necessary in many commercial applications.

The programmable action sampler system of this invention provides such versatility. It is capable of storing a large number of discrete samples in any one of a matrix of sample cups, the system addressing independently each such sample cup in an arbitrary sequence. Furthermore, the system is relatively small in size, quick in operation, and capable of accurately indexing any of the numerous sample cup positions. More specifically, the system will accept liquid samples flowing in sequence through up to six tubes, dispensing these samples into various sample cups. At a later time determined by the operator, the system will automatically address each sample, for measurement or further processing, employing a cannula for this purpose. Between operations, the cannula is bathed constantly to prevent the previous sample from contaminating the next sample. All of the many sample positions are capable of being held at a constant temperature. Moreover, the system is relatively simple in construction and versatile in operation. These and other objects and advantages of the invention will be apparent to those skilled in this art from the following description of a preferred embodiment of the system.

BRIEF SUMMARY OF THE INVENTION

A programmable action sampler system is described which includes a sample head supported on a structure movable in two orthogonical directions, referred to as the X and Y axes. Mounted beneath the sample head to receive, store, and deliver samples is a matrix of individual sample cups. Carriage means are provided to position the head over any selected one of the sample cups, permitting samples to be dispensed from the head into the cups or to be withdrawn from the cups by the sample head through a cannula. Bath means are included to wash the cannula between sample operations, the cannula preferably being immersed in a continuously flowing wash bath between sample operations. Also, preferably the carriage means includes means to accurately locate the carriage over any given sample cup, this means including a blade brake co-operating with notches in a brake rail, the blade brake upon actuation placing the blades into position to be received in a selected notch of the brake rail to accurately locate the sample head relative to any given sample cup. While in the preferred form the cannula includes a vacuum line for withdrawing the sample from the sample cup, in another embodiment the cannula may include a probe for measuring the state of a reaction proceeding in the liquid sample held in any given sample cup.

BRIEF DESCRIPTION OF THE DRAWINGS

The invention will be further described in connection with the accompanying drawings in which.

DETAILED DESCRIPTION

Figure 1:
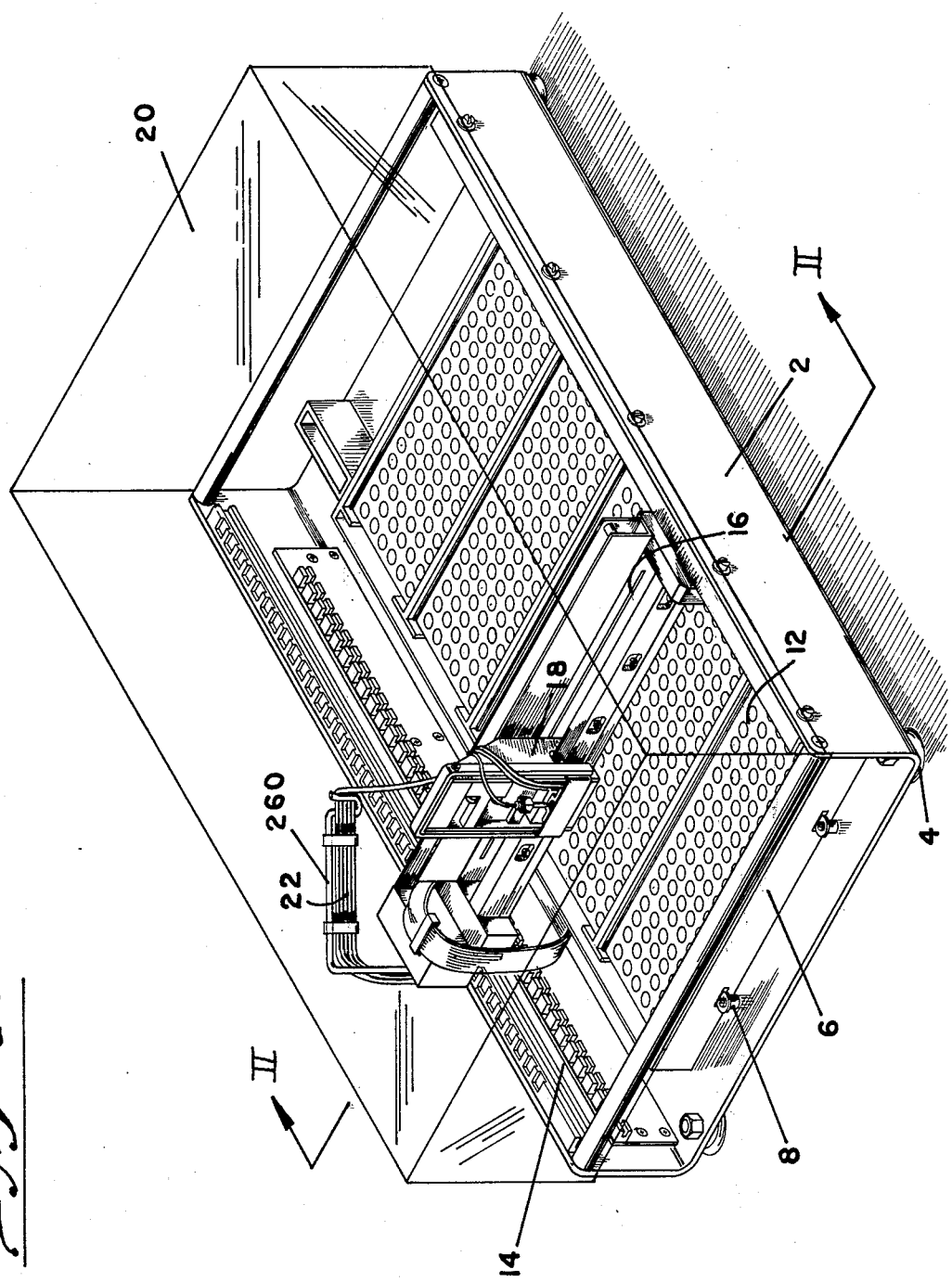
FIG. 1 is a perspective view of the programmable action sampler system.

As has been stated, the programmable action sampler system (PASS) is designed to dispense a liquid sample flowing in sequence through a tube into any one of a matrix of sample cups, then, at a later time, to operate on that sample, the samples being randomly addressable by the system. A system which possesses this capability is illustrated in FIG. 1. The various components of the system are mounted within a base 2, this base in turn being supported on a horizontal surface by footpads 4 that are threadable received in the base, one at each corner, for adjustment to seat on a horizontal surface. Within the base is a tray 6 that is removably attached to the base by cams 8 attached to the base and rotatable to interlock with slots in the tray. The tray receives a matrix of sample cups in assemblies 12, each assembly being independently removable from the tray. Along opposed sides of the base are mounted rails 14 along which rides a carriage 16, called the "Y" axis carriage, this carriage in turn supporting the sample head 18. A transparent cover 20 removably rests on the upper edges of the base. By energizing the motors driving the carriage along the rails and the sample head along the carriage, the sample head may be positioned over any selected sample cup position in tray 6. Thus, liquid samples flowing to the sample head through sample lines 22 may be dispensed in the sample cups, and selected samples in the cups may be addressed by the cannula incorporated in the sample head and withdrawn into sample lines 22 for further analysis or disposal.

As can be appreciated from even this brief description of the system, its construction involves a number of sub-assemblies and components. These sub-assemblies and components are illustrated in the other figures of the drawings. Many sub-assemblies and components incorporate standard mechanisms and structures used in other environments and applications. Since they are well known to those skilled in this field, they will not be described in detail. Rather, only their type and particular, unique interrelationships will be set forth.

Figure 2:
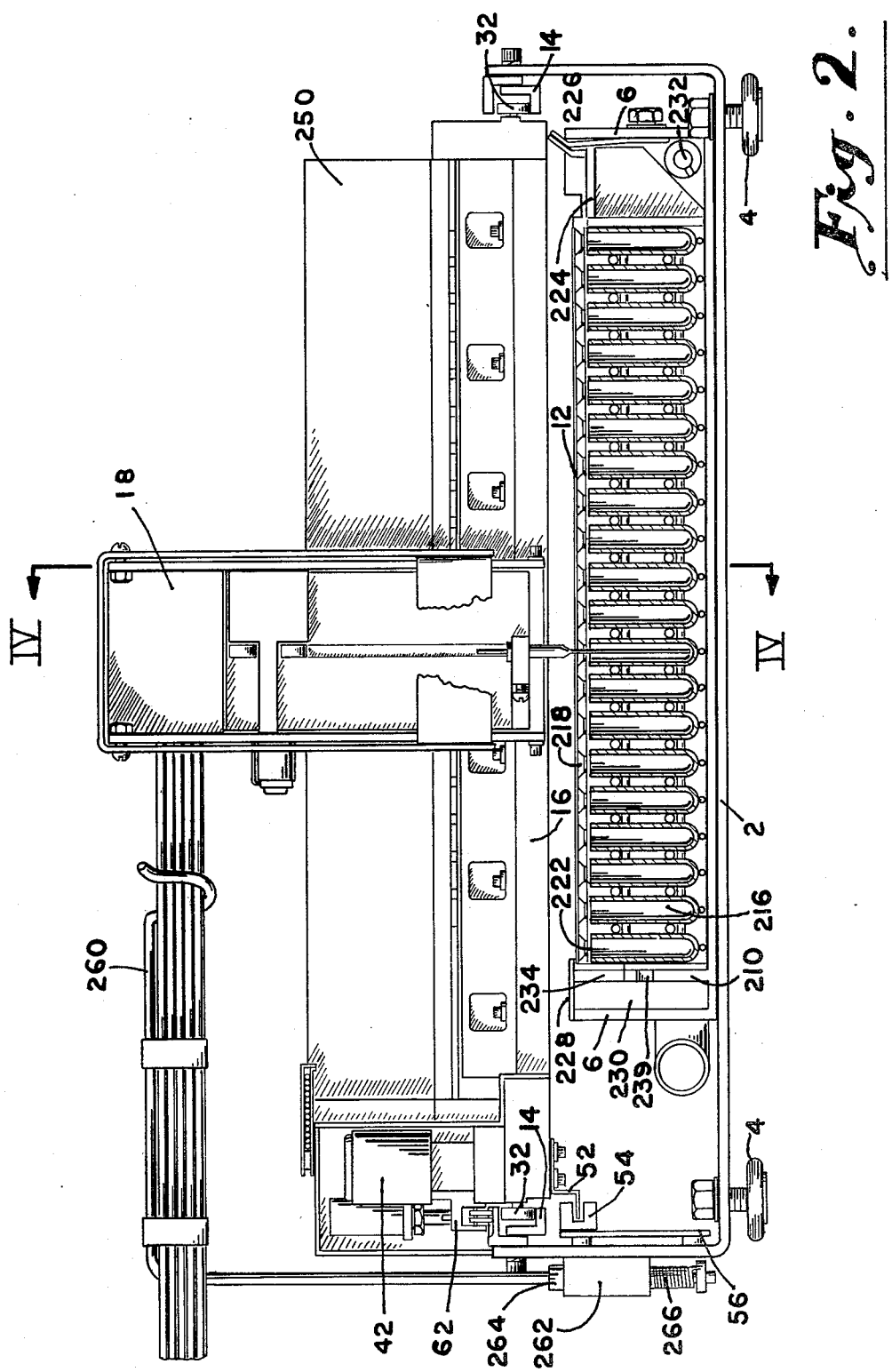
FIG. 2 is a view of the system (with the cover removed) in vertical cross section along the plane defined by lines II—II of FIG. 1.
Figure 3:
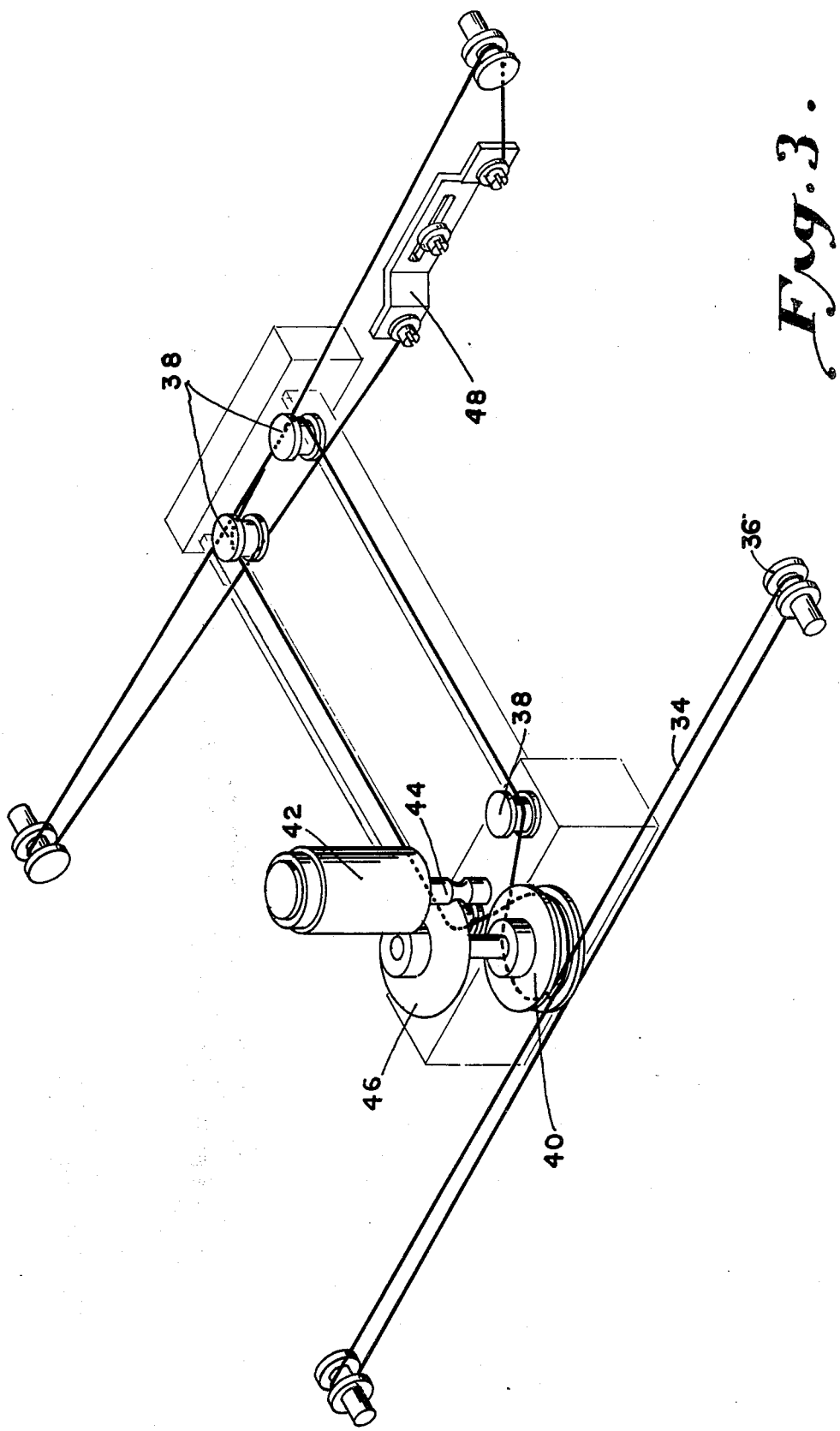
FIG. 3 is a schematic view of the X-axis drive assembly.

As shown in FIG. 2, the "Y" axis carriage 16 is mounted on bearings 32 that ride on rails 14. The mechanism for driving the "Y" axis carriage along the "X" axis rails, as shown in FIG. 3, incorporates a cable 34 that is positioned about cable guides and clamps 36 to the base adjacent the ends of the "X" axis rails and rollers 38 within the "Y" axis carriage, including a drive pulley 40. The "X" axis drive motor 42 causes a projecting drive shaft 44 to rotate, this drive shaft including an hourglass-shaped portion that engages drive wheel 46. This shape of the reduced portion of the drive shaft provides substantial stiffness to the shaft while also matching the shape of the rim of drive wheel 46. The drive shaft is placed in firm engagement with the drive wheel by its assembly within the end portion of the "Y" axis carriage, which is feasible because of the stiffness of the shaft. This firm engagement causes the drive shaft of the "X" axis drive motor to drive wheel 46 in the direction determined by the rotation of the drive motor, this direction and rotation being reversable and determined by the electrical potential supplied to the "X" axis drive motor. As the "X" axis drive motor turns, it causes the drive wheel 46 to rotate drive pulley 40, as indicated, this pulley in turn causing cable 34 to be moved through the "Y" axis carriage and both ends of the carriage to be moved along the "X" axis rails at a uniform rate. A cable termination and adjustment member 48 also is provided.

Referring again to FIG. 2, as the "Y" axis carriage moves along the "X" axis rails, an "X" axis flag member 52 attached to the underside of the "Y" axis carriage passes between a series of optical sensors 54 attached to a printed circuit card 56 mounted to the side of base 2. These optical sensors are located in line with columns of the sample cups in sample cup assembly 12, as illustrated in FIG. 1, there being an optical sensor pair for each column of sample cups and the vacant columns occupied by the side walls of the sample cup assemblies. Each optical sensor pair includes both a light-emitting element and a light-sensitive element. As the "X" axis flag 52 passes between each optical sensor pair, it physically interrupts the light path between the light-emitting and light-sensitive elements of the optical sensor pair. Thus, a signal is supplied to the associated control system indicating in positive fashion the position of the "Y" axis carriage along the "X" axis rail.

When the "Y" axis carriage has reached a desired sample cup column or line, as generally indicated by interruption of the light path between the optical sensors associated with that sample line, the associated control system (which will be subsequently described) preferably slows the "X" axis drive motor to slow the motion of the "Y" axis carriage along the "X" rail, then engages the "X" axis brake assembly 62. This assembly is best illustrated in one of the figures illustrating the sample head assembly (FIG. 7), and therefore will be described subsequently and in detail in connection with that assembly. Because of the construction of this brake assembly, it accurately locates the sample head over the desired column of sample cups.

Figure 4:
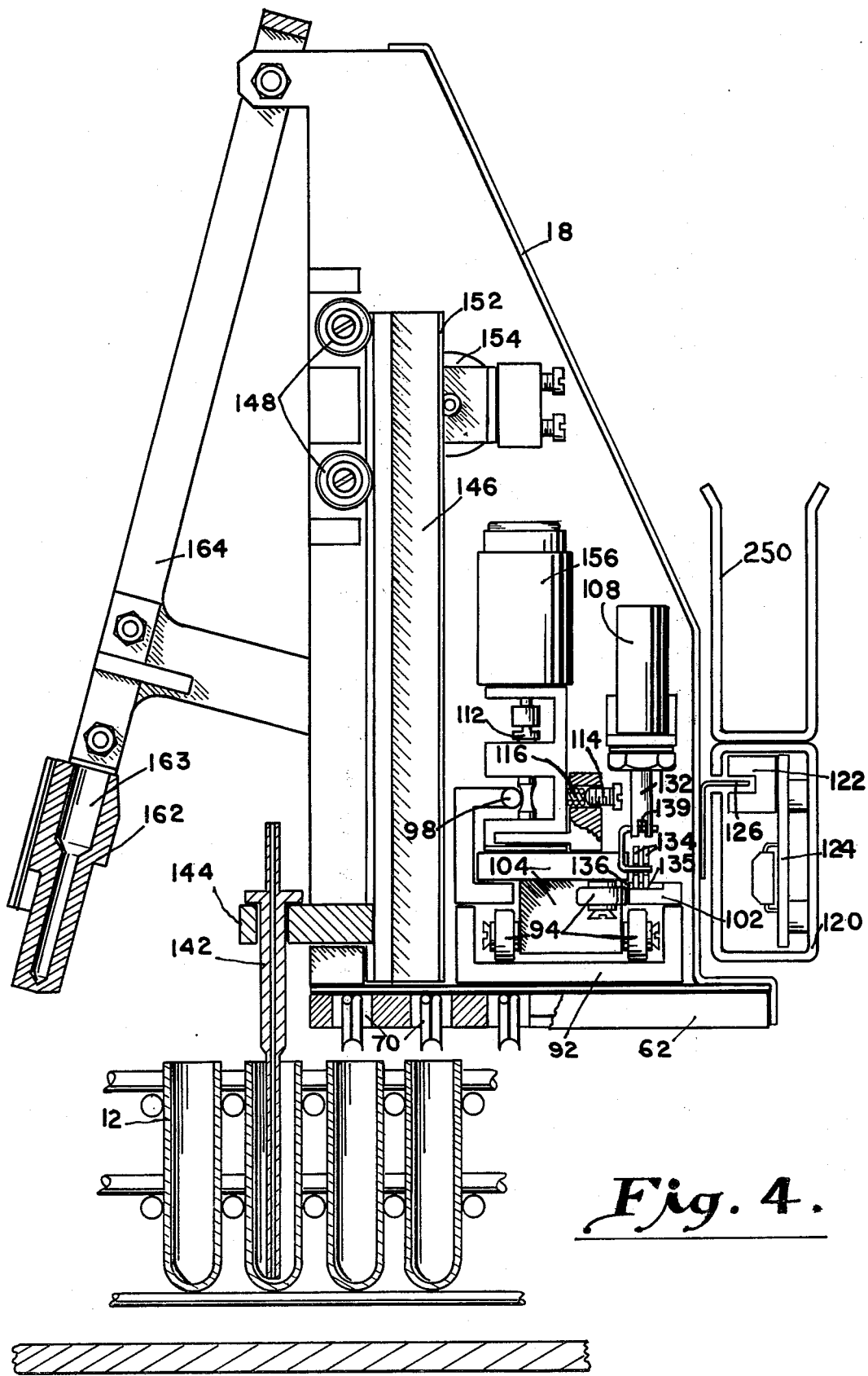
FIG. 4 is a view of the sample head and tray in vertical cross section taken along lines IV—IV of FIG. 2.

As the "Y" axis carriage moves along the "X" axis rail, simultaneously the sample head preferably is driven along the "Y" axis carriage. The various components of the sample head assembly, and the association of the sample head assembly with the sample tray is best illustrated in FIG. 4. The sample head includes, mounted along its base, a sample dispenser 62 shown in perspective in FIG. 5. That dispenser incorporates an inlet assembly 64 including six inlet tubes 66, each tube being connected to a dripper tube 68. These dripper tubes are received within opening 70 spaced along the body of the sample dispenser and aligned over sample tubes as shown in FIG. 4 when the sample head is in position for a dispensing or sample-withdrawing operation. Adjacent to each dripper tube is a vacuum tube 72 which is in turn connected by a piece of flexible tubing to an outlet assembly 74 consisting of a series of outlet tubes 76. The dripper tube 68 and the vacuum tube 72 are coated with a hyrophobic coating 69 such as teflon to prevent any "wicking" of the sample up the exterior sides of the tubes. These outlet tubes are in turn connected by flexible tubing (not illustrated) to the inlet tubes 82 of a vacuum waste manifold 84 illustrated in FIG. 6. While this vacuum waste manifold may be incorporated within the sample head, to limit the mass and thus the power required to drive the sample head, preferably this vacuum waste manifold is attached either to the base of the system, or the outlet tubes are led to an associated system incorporating the vacuum waste manifold. In either event, connected to the vacuum waste manifold 84 is a vacuum line 86 that may be selectively energized. For example, the vacuum line may be connected to a vacuum pump that is selectively energized, or the vacuum line may be connected to a valve which in turn is connected to a vacuum source, the valve being actuated to apply vacuum to line 86. In either event, upon application of a vacuum to the vacuum line 86, a vacuum is in turn applied through the vacuum waste manifold 84 to inlet tubes 82, and by the flexible tubing connecting them to outlet tube 76 in turn to vacuum tubes 72, a vacuum tube being associated with each dripper tube 68.

Figure 5:
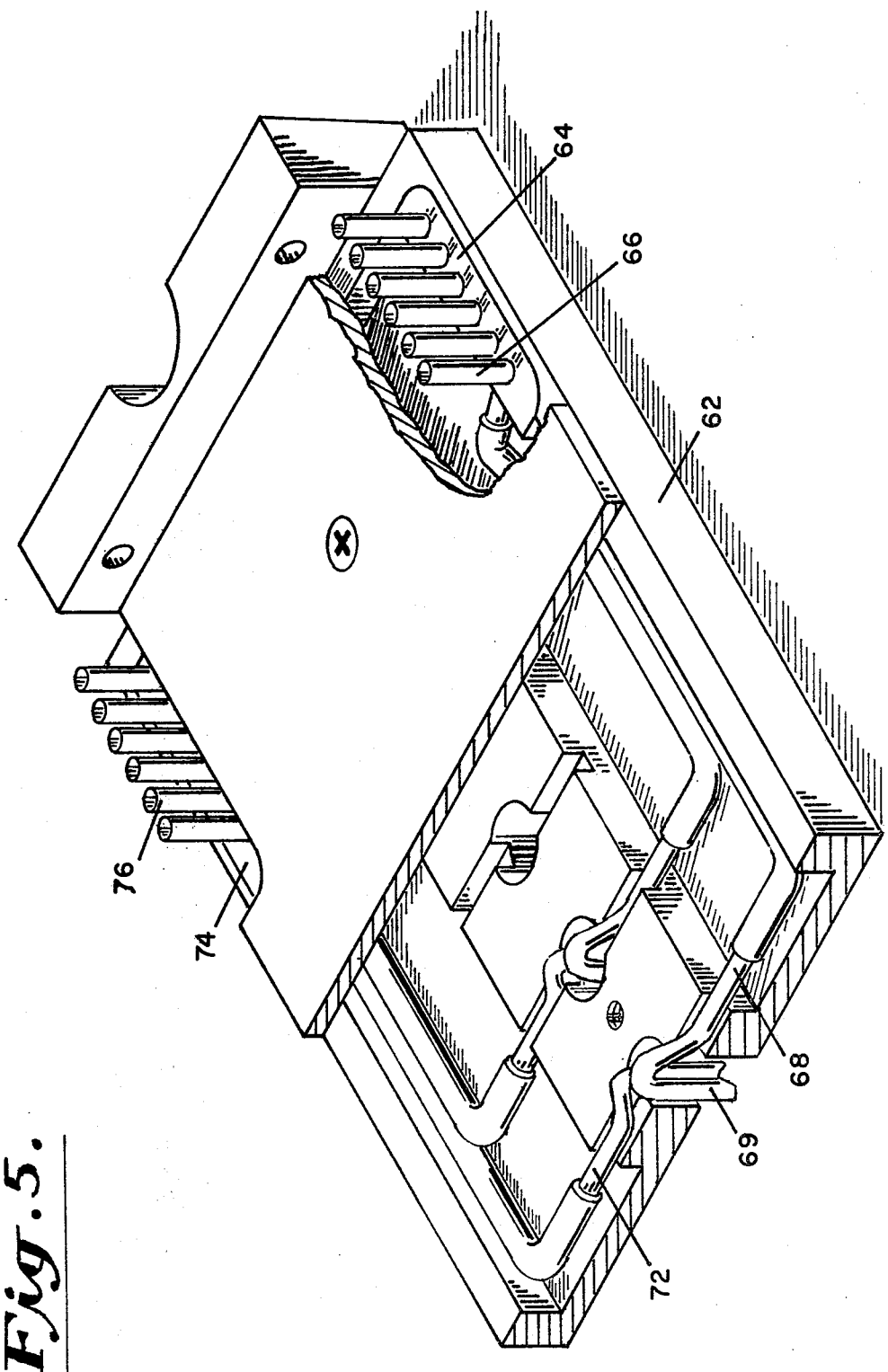
FIG. 5 is a perspective view of the sample dispenser incorporated in the sample head.

In the preferred system, liquid samples are sequentially supplied in parallel sets to the inlet assembly 64 of the sample dispenser 62 of FIG. 5 through a series of tubes, these liquid samples being separated by air bubbles. For example, such samples may be supplied from a conventional peristaltic pump such as manufactured by the Technicon Corporation. Each liquid sample preferably is isolated from the next liquid sample by a series of wash or isolation liquid samples, the purpose of these samples being to prevent contamination of the liquid sample by samples which previously flowed through the tubing. As these isolation liquid samples appear at drippers 68, a vacuum is applied to the vacuum waste manifold 84 causing vacuum tubes 72, one adjacent each dripper, to cycle the isolation sample directly from dripper tube 68 into vacuum tube 72 and thus into the vacuum waste manifold 84. As successive samples reach the dripper tube 68, the vacuum applied in the vacuum waste manifold is terminated, permitting the vacuum waste manifold to reach ambient air pressure, and thus the liquid samples to drip from dripper tube 68 into the associated sample tubes, one beneath each dripper as illustrated in FIG. 4. Preferably the flexible tubing connecting the inlet tubes and outlet tubes to the drippers and vacuum tubes are short lengths of Tygon tubing. Also, preferably the dripper and vacuum tubes are formed of stainless steel and are silver soldered together, the adjacent openings of the dripper and vacuum tubes being shaped as illustrated in FIG. 5 to enhance the flow of the sample from the dripper tube to the vacuum tube. Because of the very small diameter of the dripper tubing, the effects of capillary action will tend to affect the formation of drops at the end of each dripper. For a very small dripping port, the drops and their associated bubbles may tend to climb up the dripper rather than fall down into the intended receptacles. In the preferred embodiment, these drippers are coated everywhere with a hydophotic substance 69 such as teflon, thereby defeating the effects of capillarity and providing a good, well defined drop. Also, preferably the entire sample dispenser assembly is formed as a single unit, as illustrated, simplifying its inclusion as a component of the sample head.

The sample head, as shown in FIG. 4, is mounted to roll along a U-shaped channel 92, the sample head structure being supported on this channel by bearings 94. Mounted on one side of the channel 92 is a second U-shaped channel 96 incorporating at its upper end a stainless steel rod 98. Mounted on the other arm of the U-shaped channel 92 is a wide brake rail 102. The "Y" axis carriage block 104, to which the bearings 94 are attached, carries on its upper surface the "Y" axis drive motor 156 and the "Y" axis brake solenoid 108. The "Y" axis drive motor drives a shaft 112 which in turn bears upon the stainless steel rod 98, the rod engaging an hourglass shaped portion of the drive rod 112. The assembly to which the "Y" axis drive motor 106 is attached is in turn adjustably connected to the "Y" axis carriage block, the "Y" axis carriage block including an adjustment screw 114 bearing upon spring 116 to urge the "Y" axis drive motor assembly into firm engagement with the stainless steel rod 98 on U-shaped bar 96. Thus, by supplying an electric potential to the "Y" axis drive motor, its drive shaft will rotate against the stainless steel rod 98 to drive the sample head along the "Y" axis carriage in the direction determined by rotation of the "Y" axis drive motor.

Figure 7:
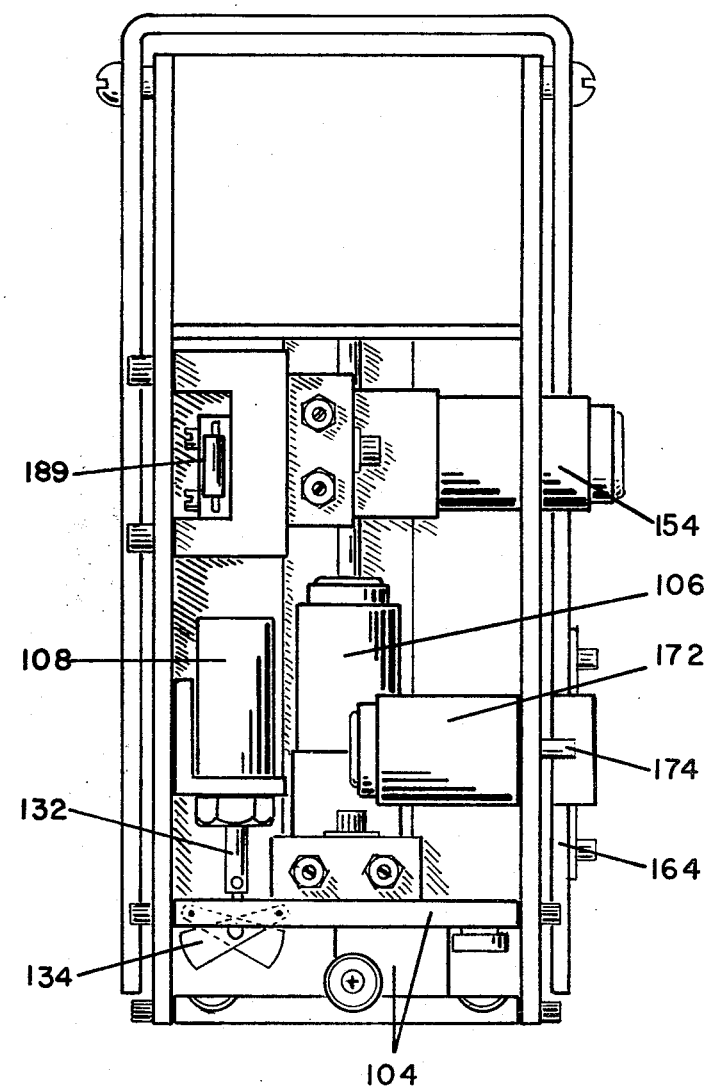
FIG. 7 is a vertical view of the sample head with the cover removed and showing the relative positions of the various major components within the head.

Attached to the "Y" axis carriage, as shown best in FIG. 4, is a housing 120 incorporating a series of optical sensor pairs 122 mounted on a printed circuit card 124 which in turn is attached to channel 120. A "Y" axis flag 126 is attached to the exterior of the sample head structure, this flag passing through an opening in channel 120 and between the light-emitting and light-sensitive elements of each optical sensing device as the sample head moves along the "Y" axis channel 92. Thus, in a manner similar to the "X" axis position sensor, the "Y" axis position is sensed in a positive fashion by interruption of the light path between the elements of the optical sensing device during passage of flag 126, this interruption being signalled to an associated control system through the "Y" axis printed circuit card 124. The optical sensing devices are each in line with a row of sample cups in the sample cup assembly 12. As the sample head reaches the desired position, as signaled to the associated control system by the appropriate optical sensing device, preferably the speed of the sample head is slowed by reducing the potential applied to the "Y" axis drive motor, and the "Y" axis brake solenoid 108 is actuated (actually de-energized). This brake solenoid is best shown in FIG. 7. Upon being actuated, the shaft 132 of "Y" axis brake solenoid moves upwardly. This shaft in turn is connected to a pair of brake blades 134. These brake links are pivotally mounted at their ends to the "Y" axis carriage block 104, connected to the sides of the sample head assembly.

As shown in FIG. 4, the "Y" axis brake solenoid is attached to the sample head assembly with the brake blades 134 positioned over brake rail 102. Brake rail 102 consists of a series of depressed pads 135 separated by ridges 136, this defining a castellated bar. When the sample head, driven along the carriage rail by drive motor 106, reaches the desired row of sample cups, as indicated by flag 126 braking the light path of the associated optical sensor pair 122, the "Y" axis brake solenoid 108 is de-energized to drop blades 134 onto the pad 135 between ridges 136. Preferably, as the sample head approaches this position, indicated by flag 126 braking the light paths of the sensor pairs adjacent the optical sensing device 122 associated with the desired row of sample cups, the electrical energization of the drive motor 106 is reduced by the electrical control system to slow the sample head. Upon brake solenoid 108 being de-energized and blades 134 dropping to the pad between ridges 136, further motion of the sample head will cause one of blades 134 to engage an associated ridge 136. Then, preferably the electrical system energizes the drive motor 106 to move the sample head in the opposite direction, causing the other of brake blades 134 to engage the other ridge 136 defining the pad over the desired row of sample cups. In this manner, the sample head is centered accurately over the desired row of the sample cups by engaging the pair of brake blades 134 with the ridges defining the pad over the desired row of sample cups.

The manner in which from one to six liquid samples are dispensed into the sample cups by sample dispenser 62 already has been described.

To withdraw a sample from a sample cup, cannula 142 is employed. This cannula in turn is attached to an arm 144 of a T-shaped (in horizontal cross section) cannula carriage 146, the cannula carriage riding upon cannula bearings 148 mounted between the sides of sample head 18. Along the base of the T-shaped carriage is attached a stainless steel rod 152. The drive shaft of cannula drive motor 154 engages this stainless steel rod in a portion of reduced cross section, similar in shape to the reduced, hourglass cross section of the drive shaft 112 connected to the "Y" axis drive motor 106 and the drive shaft 44 of "X" axis drive motor 42. Preferably, the cannula drive motor support is adjustable to permit the drive motor to be firmly engaged with the stainless steel rod 152 of the cannula carriage 146. By energizing the drive motor, the cannula carriage may be caused to move in a vertical plane either up or down relative to the sample cups.

Figure 8:
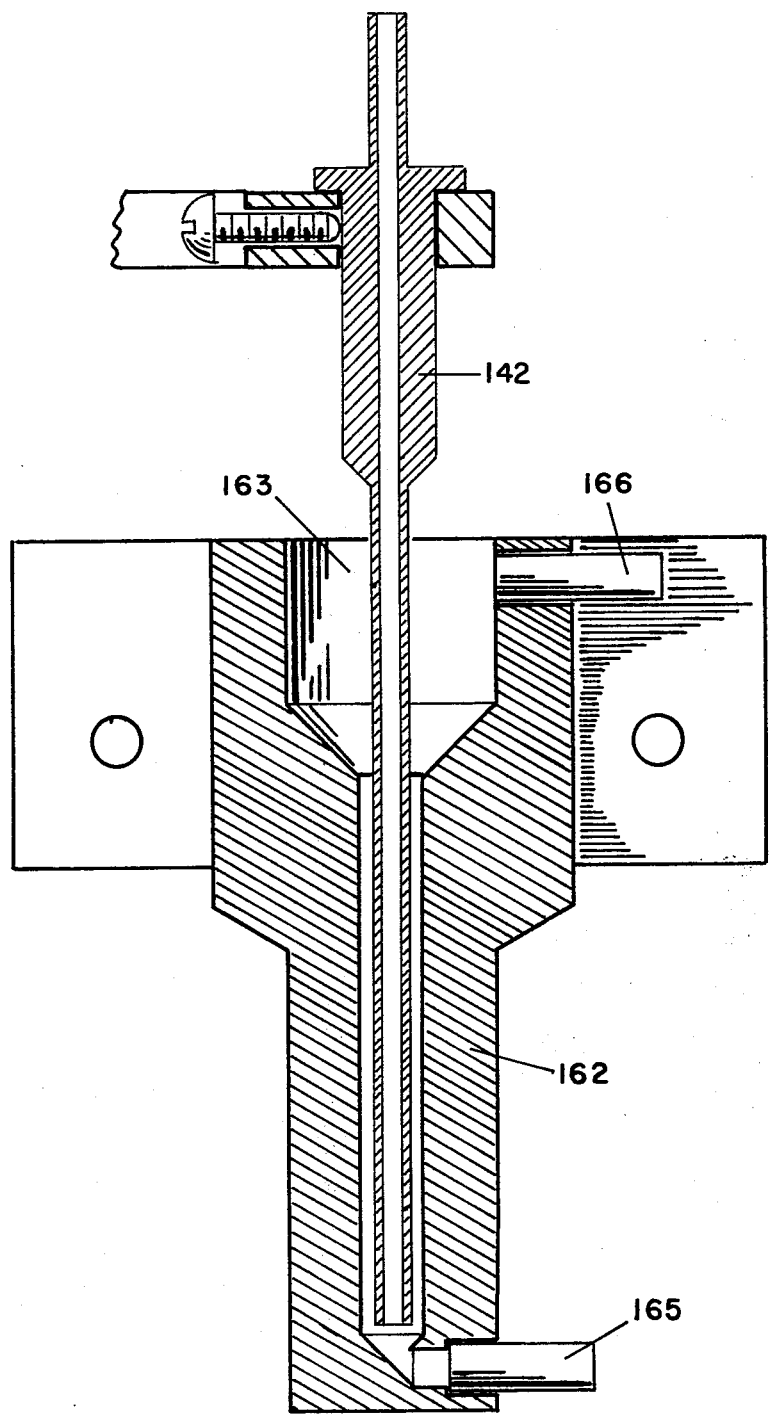
FIG. 8 is a view in vertical section of the cannula and its associated wash bath housing.

While the sample head is moving between sample cup positions, the cannula 142 is received in a wash bath housing 162 containing a central cavity 163 and mounted on an arm 164 pivotally attached to a tab at the upper end of the sample head 18. The associaton of the cannula with this wash bath housing is best shown in FIG. 8. The interior cavity of the wash bath housing is shaped to receive the tip of the cannula and to provide an enlarged well adjacent the upper end of the cavity. An inlet tube 165 communicates with the lower end of the opening 163 and the wash bath housing, and an outlet tube 166 communicates with the upper end of the enlarged top portion of opening 163. A wash bath solution continuously is applied through a flexible tube (not shown) to inlet tube 165. A vacuum is applied to outlet tube 166 through a flexible tubing (not shown). Thus, when cannula 142 is not present within opening 163, the wash solution flows upwardly within opening 163 until it reaches outlet 166 and is withdrawn. Upon insertion of cannula 142 into the wash bath housing in a manner which will be described, the exterior of the cannula is washed by the wash solution already within opening 163 and which continues to flow through opening 163 from inlet 165 to outlet 166. Upon application of a vacuum to cannula 142 through a flexible tube (not shown) connected to the cannula at its upper end, wash solution is drawn through the cannula and the associated flexible tube to wash the interior of the cannula and sample withdrawal system, preventing contamination of a subsequent sample by a previous sample.

Figure 9:
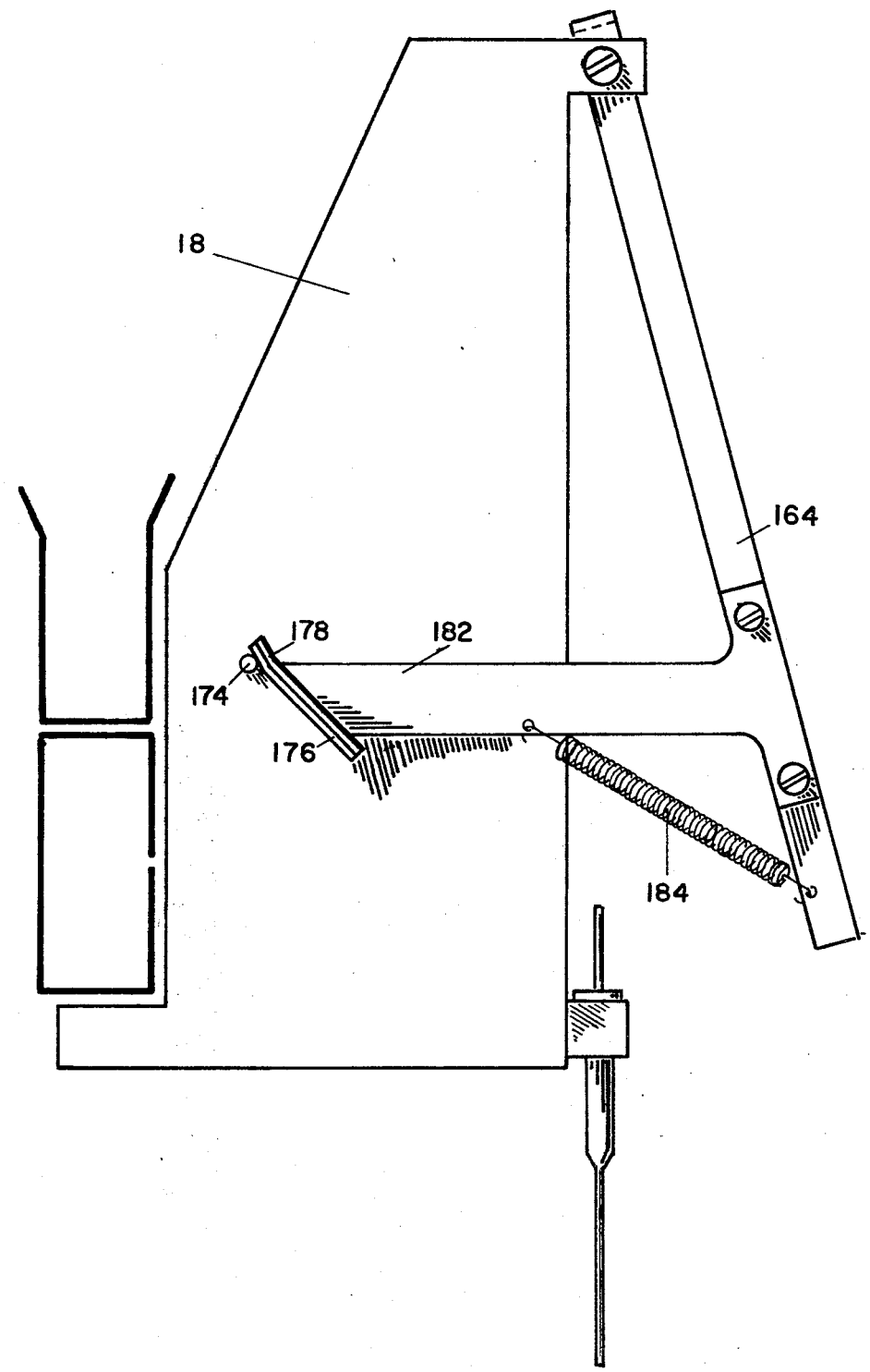
FIG. 9 is a side view of the sample head.

Upon reaching a desired position, the cannula drive motor within the sample head 18 is energized to move the cannula upwardly an amount sufficient to withdraw it from the wash bath housing 162. A wash motor 172 (FIG. 7) is energized causing its associated drive shaft 174 to rotate. As shown in FIG. 9, this drive shaft bears upon a pad 176 mounted on shoe 178 connected to arm 182, which arm in turn is attached to frame 164. A spring 184 attached between arm 182 and frame 164 causes pad 176 to bear firmly against the drive shaft. Thus, when the wash motor is energized, its drive shaft causes frame 164 and its associated wash bath housing 162 to be moved out and away from cannula 142. Preferably, the upper tip of the brake shoe and associated pad is turned upwardly as illustrated in FIG. 9. Because of this, when the motor has caused the wash bath housing to reach its outer limit of travel, the force impelling the frame 164 outwardly is directed in a more vertical direction to increase the force on shaft 124, stopping the wash motor and maintaining the wash bath housing in the extended position while the cannula operates upon the sample in a sample cup.

To withdraw a sample from a sample cup, the cannula drive motor 154 is actuated first to lift the cannula from the wash bath housing 162. Then, while the cannula is held in a raised position, the wash motor 172 is energized to move the wash bath housing 162 to its extended position. Thereafter, the cannula drive motor is energized to lower the cannula 142 into a sample cup. Preferably a cannula microswitch 189 (FIG. 7) engages detents on the base web of the T-shaped cannula carriage 146, the cannula limit microswitch 182 thereby directing the associated electrical control system to insert a resistor to reduce the current in motor 154 when the end of upward travel is reached. To lower the cannula, the motor is de-energized and the cannula falls rapidly under the breaking action of the motor's back e.m.f. After being lowered into position, a vacuum is applied to the sample line (not shown in FIG. 4) connected to cannula 142 and some or all of the sample cup is withdrawn into the sample line. Thereafter, the cannula drive motor is energized to lift the cannula from its lower position to its upper position, then the polarization of the wash motor 172 is reversed. Upon being reversed, spring 184 exerts sufficient force on arm 182 to permit motor to drive frame 164 back against the sample head housing 18. After an appropriate interval to permit this withdrawal of the wash bath housing to a position against the sample head housing, the cannula drive motor is de-energized to let the cannula descend into the wash bath housing and braked slightly by the back e.m.f. generated in the cannula drive motor.

The sample cup assembly 12, as shown in FIGS. 2 and 4, consists of a frame 210 within which are received a series of parallel wires 212 and 214, these wires together defining a matrix of spaces for receiving each individual sample cup 216. Across the top of frame 210 is a cover 218 including funnel-shaped openings 222, each opening being located over a sample cup 216. Preferably, cover 218 is received in longitudinal slots within frame 210, permitting the cover to slide away from a position over the sample cups to expose the sample cups for removal and replacement as desired. Frame 210 includes an extension 224 which, upon inserting the frame into the tray 6, cams past a tube tray retainer spring 226, the spring then overlying extension 224 to prevent its accidental removal. The opposite top end of the frame 210 underlines the top 228 of a water manifold 230. A constant temperature water inlet tube 232 runs along one inner corner of tray 6, this tube including a series of perforations permitting the water it carries to flow into tray 6 and about the sample cups. The water exit manifold 230 includes a series of openings 239 and a floodgate 234. When the sample cup assembly is removed, the water flowing from inlet tube 232 is permitted to flood the space within the tray which receives the sample cup assembly. This water flows through exit ports 239 into exit manifold 230 and water exit port tube 236. When the sample cup assembly is placed within tray 6, it covers exit ports 232. The volume of water displaced by sample cup assembly 12 causes the water level to rise and commense flowing over floodgate 234. Since exit ports 232 are blocked by the sample cup assembly 12, the water level is determined by floodgate 234 and remains constant. The volume of water in tray 6 when sample cup assembly 12 is not in place is determined by exit ports 232 and is just sufficient to cause the water level to rise to floodgate 234 when sample cup assembly 12 is inserted in tray 6 and contains a full compliment of sample tubes 216.

Regardless of the number of sample cups, the water will rise to the level determined by the case of floodgate 234, maintaining all sample cups at a given temperature throughout substantially their entire length.

If desired, tray 6 may include an extension 240 (FIG. 1) which communicates with a waste line permitting samples and sample isolation liquids flowing through the sample inlet tubes to be dispensed into a waste container when the sample head moves to the position determined by extension 240.

Preferably the electrical lines energizing the various drive motors lie within cable tray 250 mounted on the Y-axis carriage above channel 120, and in the space between tray 6 and the side of base 2 as shown in FIG. 2. It has been found that these cables should be attached to one another to define a flat plane, rather than a round bundle, for they best roll into and from their respective cable areas when so conformed. It has been found that the liquid sample tubes, however, are best fed from a point external of the housing along a tube support arm 260 (FIG. 2) to the sample head 18, this tube support arm being attached to the side of base 2 as illustrated in FIG. 2. More specifically, the tube support arm is received within a block 262 attached to the side of base 2, the tube support arm bearing a collar 264 which seats on top of block 262 and a spring 266 interlocked with the block and arm 260 to urge the tube support arm to rotate away from the sample head 18. Accordingly, as sample head 18 moves back and forth along the Y-axis carriage and the carriage moves along rails 14, the tube support arm 260 will rotate to a maximum of about 90° permitting the liquid sample tubes to move with sample head 18, yet holding these tubes well above sample cup trays 12.

Figure 10:
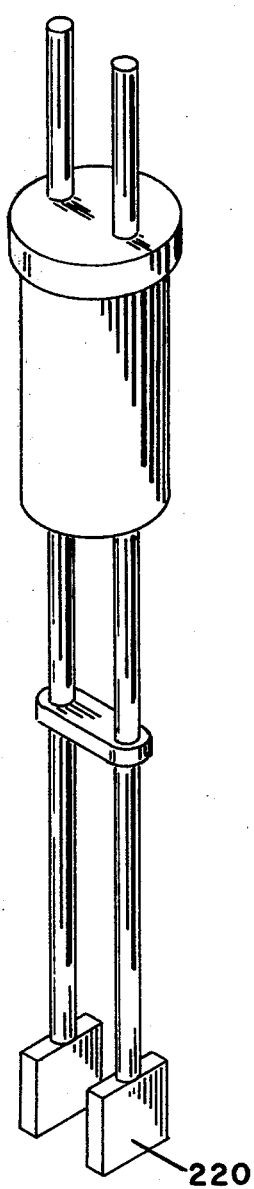
FIG. 10 is a view in perspective of an alternate sample probe structure.
Figure 11:
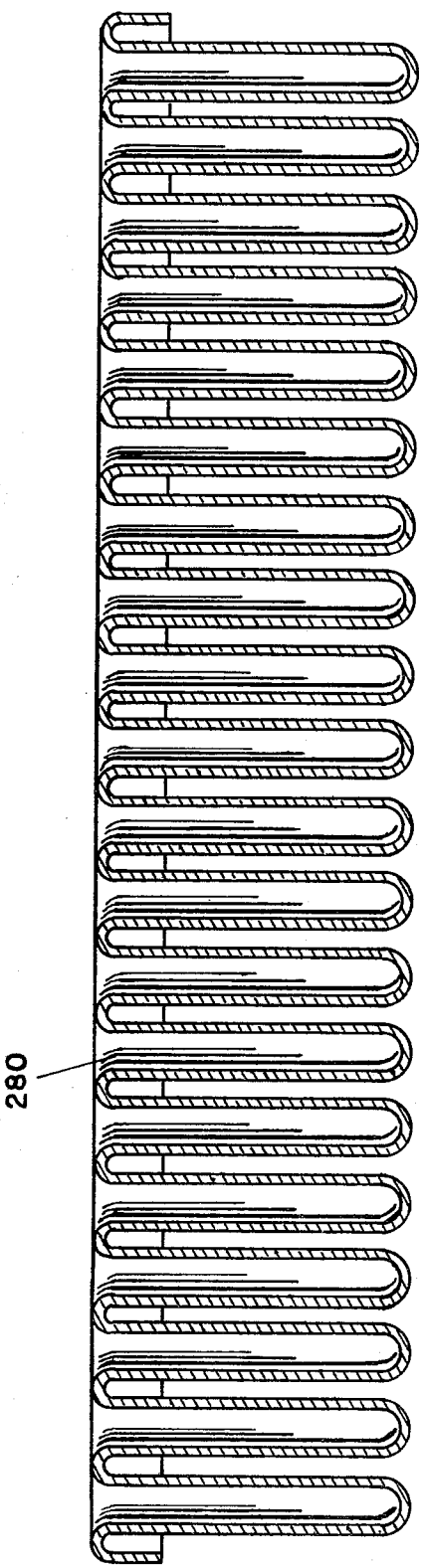
FIG. 11 is a view in vertical cross section of an alternate sample tube tray.

In the fashion which has been described, the programmable action sampler system is caused to either dispense from one to six samples into any desired single or row of sample cups, or to withdraw any desired sample from an associated sample cup. In between sample withdrawal operations, preferably the cannula 142 is continuously bathed with a wash solution. Of course, various modifications of this system will be readily apparent to those skilled in this field. For example, instead of a hollow cannula connected to a vacuum line for withdrawing samples from sample cups, a pair of probes such as illustrated in FIG. 10 may be employed as the cannula to measure the conductivity or other characteristics of the sample within the sample cup. Of course, such probes 220 also should be bathed between measurement operations. The wash bath housing would be shaped to receive these probes, and would bathe them between sample measuring operations. Further, while the sample tray has been illustrated as a series of discrete sample cups received between wire rods, it could be formed as a one-piece, molded member 280 as illustrated in FIG. 11. Fabricating the sample cups as such a unitary member significantly assists the user in cleaning the cups while not requiring him to individually position the sample cups within the wire rack forming the sample cup assembly.

Figure 12:
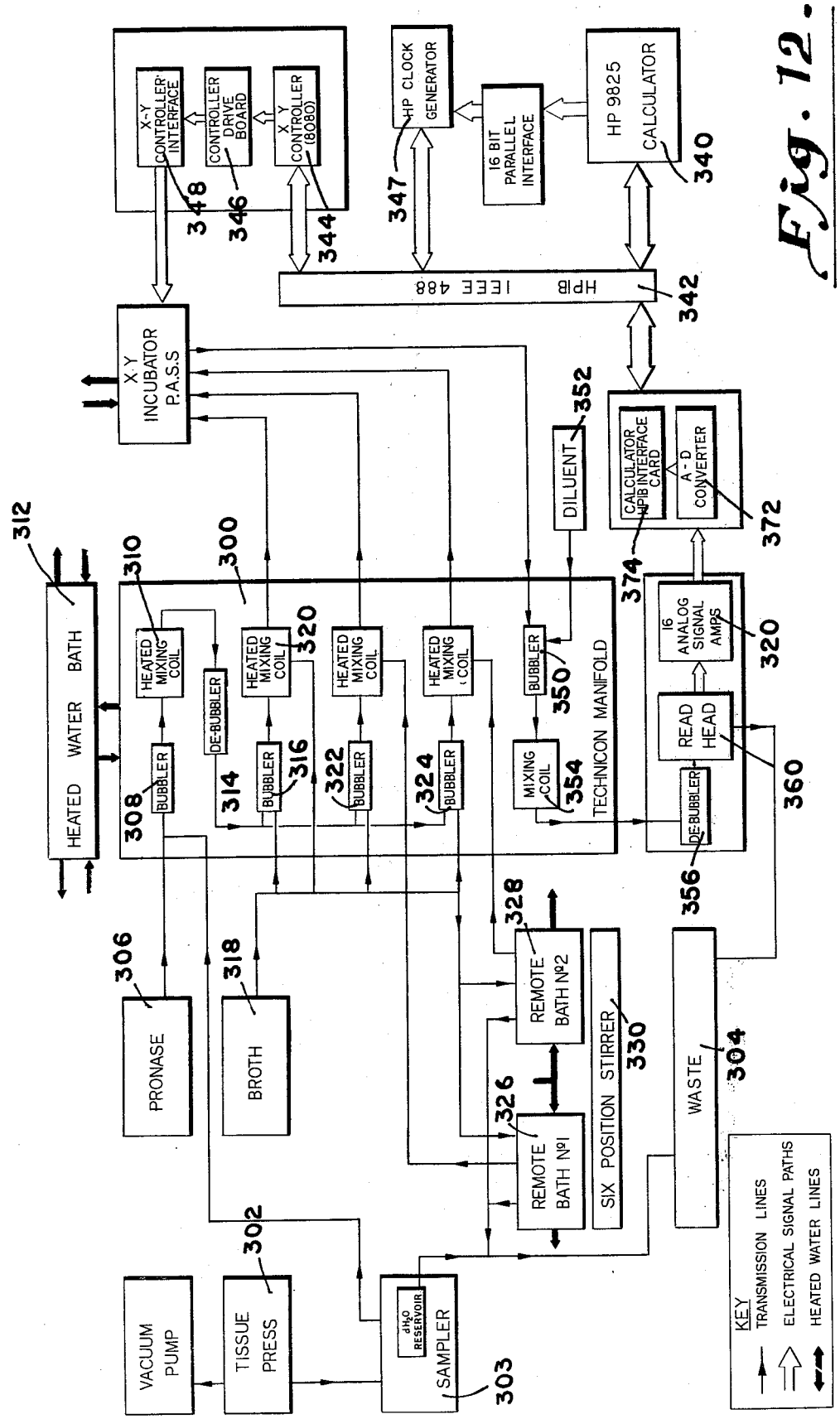
FIG. 12 is a schematic diagram of the programmable action sampler system as incorporated in a sample analyzing system employing bacterial solutions, the schematic diagram indicating the liquid transmission lines by single light lines, heated water lines by single heavy lines, and electrical signal paths by wide arrows.

In a preferred application of the programmable action sampler system as indicated in the schematic diagram of FIG. 12, bacterial samples are supplied to the system from a Technicon proportioning pump 300. The samples may be prepared by a tissue press or drainage tray 302 operated by a vacuum pump, if required, the samples being aspirated by a sample 303 and drawn from it by the pump 300. In the pump 300, these bacterial samples are combined with pronase from a source 306, the consecutive samples being separated by a bubbler 308, then applied to a heated mixing coil 310. This mixing coil is heated by water flowing from a heated water bath 312. Thereafter, the samples flow through a de-bubbler 314 and are combined in bubbler 316 with broth from a broth source 318. They then flow through the heated mixing coil 320 to the programmable action sampler system (PASS). As indicated in FIG. 12, bacterial samples may be combined with broth in bubblers 322 and 324, these samples also flowing through heated mixing coils to the PASS system. The sample flowing from bubbler 322 may be combined with a liquid flowing from a remote bath 328, these baths being maintained at a constant temperature by water supplied from heated water bath 312. If the materials in these baths are prone to settle, as is likely to be the case if bacterial samples are being supplied by these remote baths, preferably they rest on a magnetic stirrer 330 and include magnetic stirring elements within the baths to maintain the bacterial samples in uniform suspension. Broth may flow to each of these remote baths, and overflow from the baths may be dispensed to the waste trap 304 as indicated.

Figure 6:
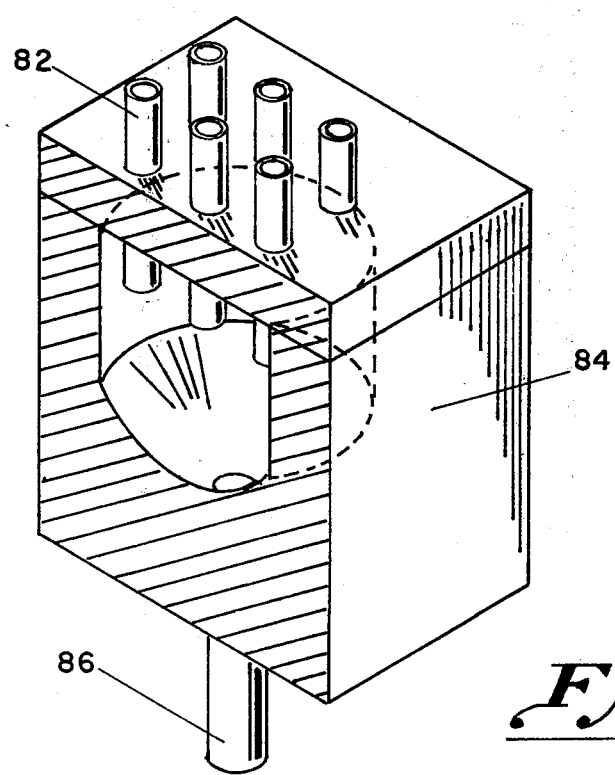
FIG. 6 is a perspective view of the vacuum waste manifold.

In the preferred system, the sampler is controlled by a computer 340 such as a Hewlitt-Packard 9825 calculator. Thus, upon placing the sample in the sampler, the operator enters sample characteristics into the calculator together with the desired reaction time and other processing information. The calculator then causes the sampler to sample this sample at the appropriate time, as determined by the availability of sample locations within the PASS, and the sample proceeds through the Technicon proportioning pump to the PASS. When the appropriate interval has occurred after sampling of the sample, this interval being determined by the time required for passage of the sample through the Technicon proportioning pump and to the PASS, the calculator 340 controls the PASS system through electrical bus 342, controller 344, containing a microprocessor, drive board 346, clock generator 347, and interface 348 to cause the sample head to be moved to the desired position. Then, calculator 340 causes the vacuum manifold line 86 (FIG. 6) to be closed, permitting atmospheric pressure to be reached within vacuum tubes 72 and the samples to drip from dripper tubes 68 (FIG. 5) into the appropriate sample cups. Upon filling the sample cups, the calculator 340 again applies a vacuum to the vacuum manifold line 86, shunting any further sample and the isolating solution between samples into the vacuum waste manifold 84 (FIG. 6). After a further interval, as determined by the types of sample information entered by the operator, calculator 340 again actuates the PASS to position the sample head over the various samples, and causes the cannula to withdraw the samples in succession. The samples preferably pass through bubbler 350 (FIG. 12) where they are combined with a diluent 352 and then to a mixing coil 354 and from there to a de-bubbler 356, read head 360, and to waste trap 304. The read head system may be any of a variety of structures. It is preferred, however, that the sample be analyzed by a differential light-scattering technique such as described by Brooks, et al., in Canadian Pat. No. 1,006,711 granted Mar. 15, 1977, or by Wyatt, et al., in U.S. Pat. No. 3,928,140 granted Dec. 23, 1975, or by Wyatt, et al., in U.S. patent application Ser. No. 716,237 filed Aug. 20, 1976, and entitled "Apparatus and Process for Rapidly Characterizing and Differentiating Large Cells".

While the patent describes a technique for analyzing discrete samples, it will be obvious to those skilled in this field how such a structure may be modified to handle samples flowing through a tube, the samples being isolated from one another by air bubbles and isolating solution as desired. The preferential light-scattering information derived from each sample by read head 360 is supplied through analog signal amplifiers 320 to an analog to digital converter 372 and then to calculator interface card 374 which in turn supplies this information to calculator 340 for analysis and display to the user. This system employing the PASS provides the user with a highly automated means for rapidly performing bioassays, for example, for anti-biotic and other selected drug and chemical residues by the process described by Wyatt, et al., in U.S. Pat. No. 3,928,140. Although the system may be run by one person, its capability of a relatively high throughput rate (e.g. 40 samples per hour) may best be utilized with two or more staff. The system is quite simple, for it continually monitors all current functions and reports on command to the operator. In addition, the system may be programmed to prompt the operator for start-up and shut-down procedures and, by means of an alarm system, to warn the operator of any detectable operator error or other system malfunction, real or potential.

As has been noted, the preferred system incorporating PASS uses a differential light-scattering bioassay technique. The actual differential light-scattering (DLS) measurement preferably employs a fine laser beam intersecting a solution. This solution contains bacteria that have been exposed to an extract suspected of containing a drug residue to which they are highly susceptible. In the read head, the capillary tube containing the bacterial suspension is surrounded by an array of detectors, each detecting light scattered at a different angle with respect to the incident beam. After suitable digital processing to remove noise and compensate for background contributions, these signals are interpolated as required to represent the DLS pattern characteristic of the bacterial scatters. This DLS pattern, shown in FIG. 2, is then compared to a pattern, the control pattern, obtained earlier from a similar bacterial suspension exposed to an extract known to be free of all potential residues. The DLS pattern changes are evaluated by means of an appropriate mathematical algorithm, and the presence or absence of drug residues are determined therefrom.

The DLS bioassay technique is a particularly powerful and efficient approach and most suitable for automation. The DLS pattern from an illuminated suspension of bacteria is a function of average cell size, size distribution, structure, and number density. Thus, any chemical agent at a concentration sufficient to affect cellular growth or morphology will yield a measurable change in the DLS pattern.

The negative screening bioassay technique incorporated in the system preferably utilizes bacterial strains found to be particularly sensitive to a wide range of antibiotics, pesticides, heavy metals, sulfas, toxins, and many other antimicrobial agents. To date, the Science Spectrum strains *Staphylococcus* 41 and *Klebsiella Pheumoniae* 886 have been found to be sensitive (in varying degrees) to most of the compounds of importance to FDA and USDA. It is extremely important to emphasize that each compound for which screening is required must be tested initially in the system using compound-fortified extracts. Dose-response curves should be run routinely to establish lower sensitivity limits and reconfirm the response and viability of the strains used.

The implementation of the bioassay screening test by means of the system is straightforward. Extracts of various tissues may be prepared by the operator from frozen specimens using the vacuum activated tissue trays or presses 302. These extracts are placed sequentially in the Technicon Sampler II, sampler 303. On command from the HP 9825 calculabor 340, each sample is aspirated, combined with pronase, and split into three parts at the Technicon manifold of pump 300. One part is then combined with an exponential phase aliquot of S. aureus 41 in bath 326, another with *Klebsiella* 886 in bath 328, and the third with a blank broth in bubbler 316. The three specimens are then thoroughly mixed in the Technicon manifold of pump 300 and stored in the water-heated PASS. After suitable incubation, the samples are sequentially aspirated and pumped through the read head 360 where their DLS patterns are recorded. These patterns are compared with similar patterns recorded earlier from control tissue extracts, and a screening report is printed out at the HP 9825 calculabor console.

All bioassay protocols, be they based on tube dilutions or agar well diffusion tests, require a detailed sequence of procedures from preparing the samples to reading the results. The approach provided by this system automates most of the steps involved, with only sample preparation and system start-up and shut-down representing the basic chores for the operator. He must, of course, maintain the system in operating order and run periodic checks to insure that all components are functioning properly. The system itself may include many built-in features to insure long and reliable usefulness. Foremost among these preferably are prompting instructions and notices displayed, as required, on the HP9825 computer console.

The system is a highly interactive one, with considerable prompting being provided the user by means of the HP9825 computer. The HP9825 preferably is programmed to contain a complete set of start-up and shut-down procedures displayed one at a time on its console for the operator to follow. Until the operator has performed each task requested, the system will not continue operation. Thus, even operators unfamiliar with programmable calculators such as the HP9825 are led through the correct sequence of steps required to properly operate the system. The operator must, of course, maintain the system in operating order and run periodic checks to insure that all components are functioning properly. The system itself has many built-in features to insure long and reliable usefulness.

As has been noted, the system consists of the seven basic subsystems. They are:

1. The Hewlett-Packard HP9825 programmable calculator 340 which contains all operating programs of the system and controls all test functions. The calculator is also attached to a digital clock and various interface busses. It includes an executive monitor which gives the operator complete overall control of the system together with status reports on command, and assists in all phases of system operation.

2. The Technicon Sampler II 303 contains a 40-sample capacity tray. The samples may be prepared by the operating staff from frozen tissues following a general protocol. After placement in a vacant tray recepticle, the identification code and sampler location are entered at the HP9825 keyboard, the "operating console". The executive monitor system of the HP9825 establishes the time of sampling and controls this function. Once a specimen has been aspirated by the sampler, the tray rotates one sample position. The remainder of the aspirated specimen may be discarded, thereby providing room for a new sample.

3. The Technicon proportioning (peristaltic) pump 300 and manifold transports and mixes all reagents used by the system. In addition to the mixing and transport of fluids, the system also provides nutrient supplies for the assay bacteria and maintains their chemostatic condition. Each sample is split into three eliquots at the manifold; one is combined with exponential phase *S. aureus*

41 with *Klebsiella* 886, and the third serves as a background blank.

4. The Lauda water heater/circulator 312 provides 38° C. recirculating water to maintain temperature in the Technicon mixing coils, the bacterial chemostat source ("bactisources"), and the programmable action sampler system where all mixed samples are incubated. A special manifold is provided for the easy connection of all water-heated systems.

5. The bacterial sources (bactisource) 326 and 328 may be mounted in individual water-heated lucite containers atop a Lab Line multi-magnetic stirring table 330. The bacterial sources contain magnetic stirrers and automatic level maintaining syphons. Syphoning and the re-supply of nutrient broth is accomplished by means of the proportioning pump.

6. The addressable X-Y incubator/sampler, PASS, may simultaneously store up to 600 samples following mixing in the Technicon manifold. The locations for the storage of each set of three aliquots (derived from each sample) are selected automatically by the Executive Monitor. Following suitable incubation, the Executive Monitor instructs the PASS to pick up each aliquot by means of its cannula 142. The proportioning pump 300 transports the samples, following dilution, to the read head 360. The 600 sample cups may be grouped into five trays of 120 cups each. Once the contents of each tray has been read, the used tubes may be disposed of and a new set of tubes loaded.

7. The read head 360 performs the DLS measurements required for screening. Following incubation, the PASS unit aspirates each sample which is then diluted and pumped through the read head 360 flow cell surrounded by a detector array of the type described in the U.S. patent by Wyatt. While the patent describes a technique for analyzing discrete samples, it will be obvious to thoss skilled in this field how such a structure may be modified to handle samples flowing through a tube, the samples being isolated from one another by air bubbles and isolating solution as desired. The preferential light-scattering information derived from each sample by read head 360 is supplied through analog signal amplifiers 320 to an analog to digital converter 372 and then to calculator interface card 374 which in turn supplies this information to calculator 340 for analysis and display to the user.

Figure 13:
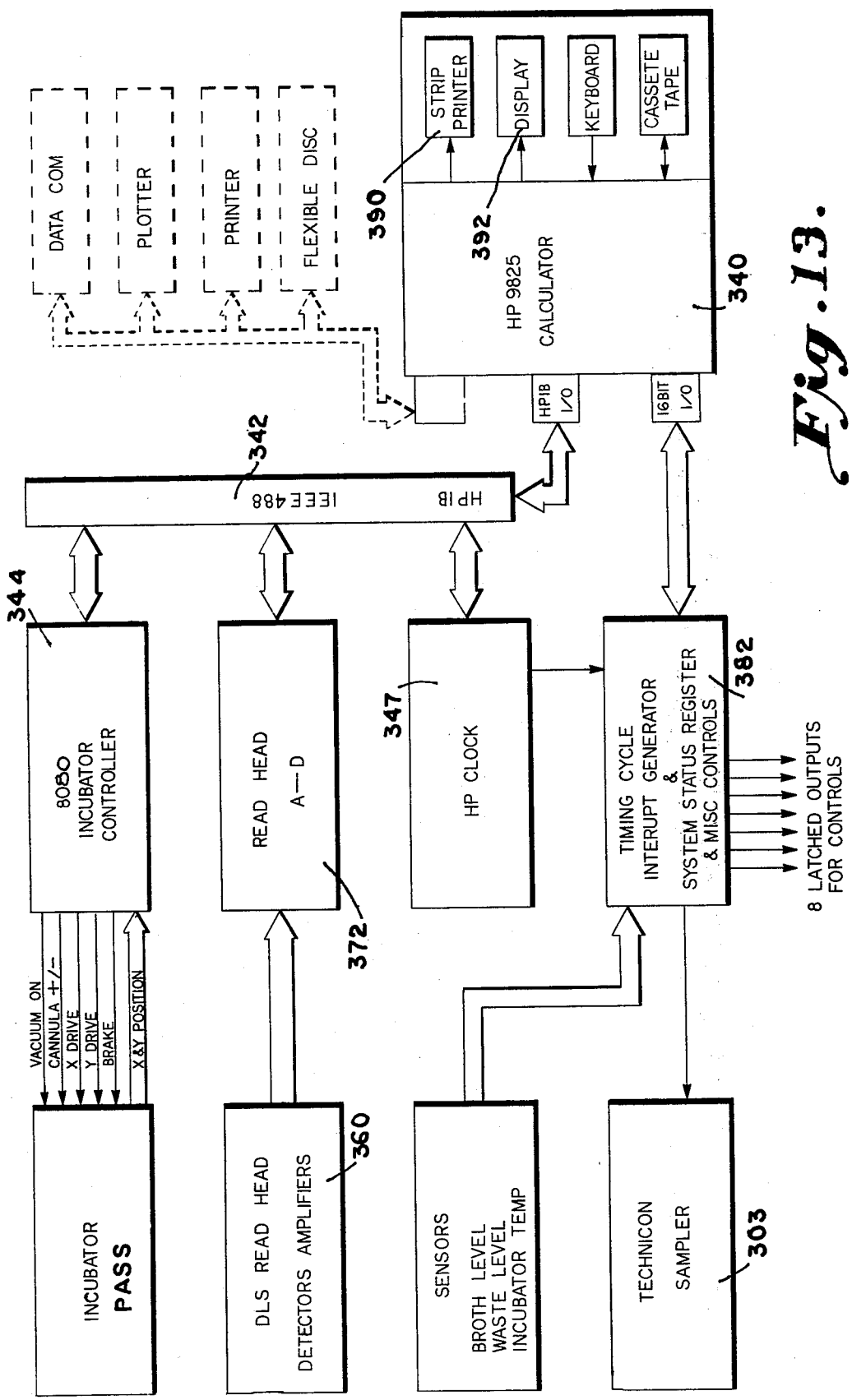
FIG. 13 is an electrical schematic diagram of the association of the programmable action sampler system with other components indicated in FIG. 12.

The electrical system of the PASS is schematically illustrated in FIG. 13. As has been noted, the calculator 340 drives the PASS system through controller 344, the controller supplying various drive and controlling signals to the PASS, such as the vacuum, cannula, X-drive, Y-drive, and brake signals. The PASS supplies "X" and "Y" position information to the controller. Read head 360 supplies differential light-scattering data to the analog to digital converter 372 which in turn supplies this information over bus 342 to the calculator 340. Various sensors may be employed in the remote baths 326 and 328. For example, they may sense the level in waste trap 304 and the temperature supplied by the heated water bath 312 to the Technicon proportioning pump 300 and to PASS, this sensor information being supplied through a timing cycle interrupt generator 382 to the calculator 340. The Technicon sampler 303 also is actuated by the calculator 340. Appropriate clock signals are applied from a clock generator 347 to the calculator through bus 342 and to the timing cycle interrupt generator 382. In addition to providing output on a strip printer 390 and display 392, the calculator 340 also may store data or provide output data on a floppy disc, printer, plotter, or data communication channel as desired by the user. The calculator includes as inputs both a keyboard and a cassette tape unit, as has been noted.

The controller for the Programmable Action Sampler System consists of five functional elements. They are: (1) a general purpose microcomputer 344 (8080 with 2000 bit ROM and a 1000 bit RAM); (2) X & Y axis position sending circuitry; (3) X & Y axis motor drive circuitry; (4) X & Y axis breaking circuitry; and (5) an interface between the S100 standard computer bus and the IEEE standard 488 communications bus. The manner in which each of these five elements functions now will be described, then the manner in which they perform in concert to control the X and Y axis positioning of the sample will be explained.

Figure 14:
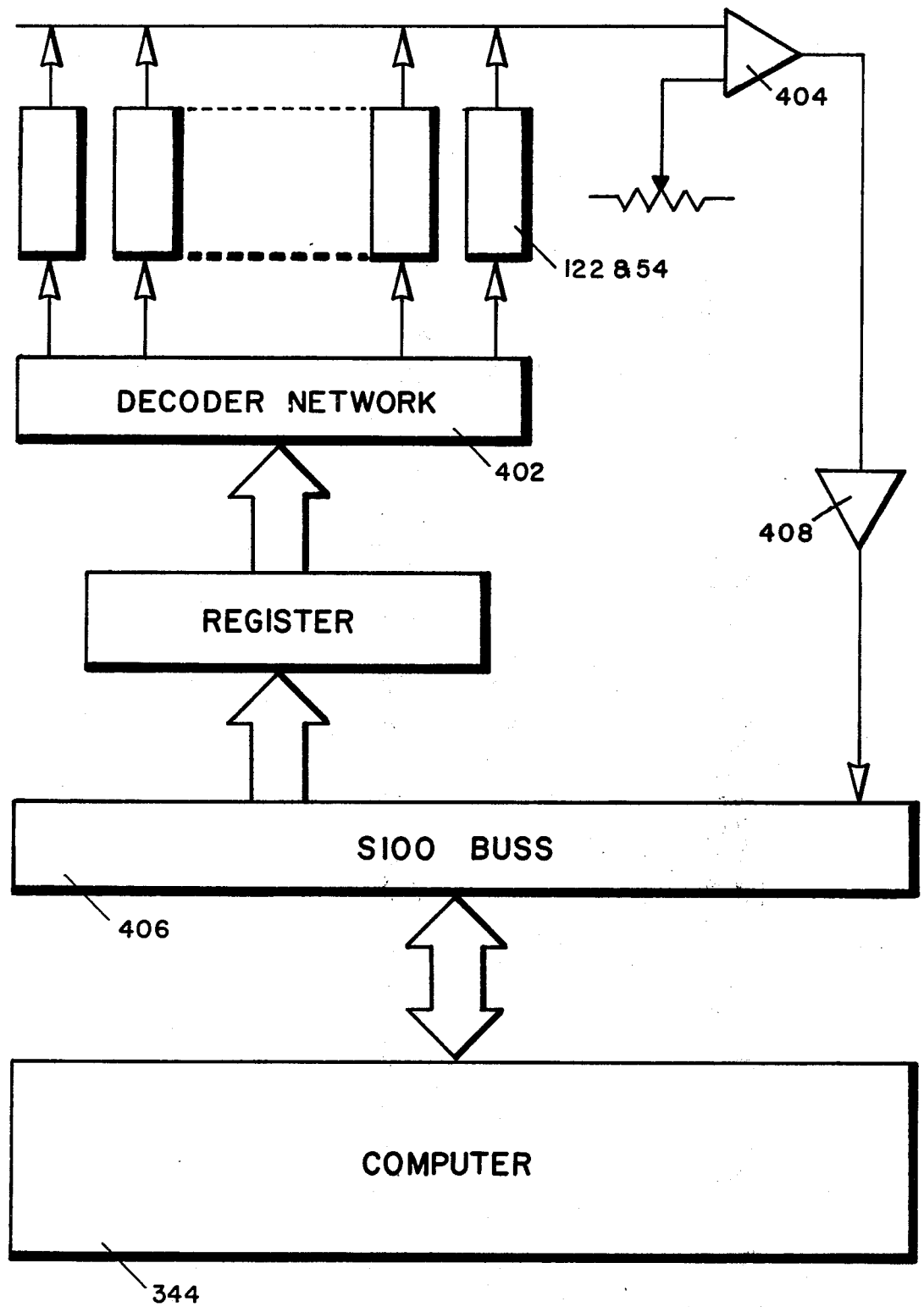
FIG. 14 is a schematic diagram of the position sensing circuitry.

The general purpose microcomputer element 344 consists of a standard 8080 microcomputer circuit board such as made by Vector Graphics, Inc., and a RAM circuit board also by Vector Graphics, Inc. This board contains 1 kilobyte of random access statis read/write memory and sockets for 2 kilobytes of EPROM (1702A) read only memory. In addition, a chassis, motor board and unregulated power supply comprise the foundation hardware which support the various circuit boards. The position-sensing circuitry for the X axis is the same as that for the Y axis. This description will address only the X axis circuitry with the understanding that the circuitry is repeated for the Y axis. As shown in FIG. 14, the major elements for position sensing are the collection of optical switches 122 and 54, a binary to unitary decoding logic network 402 and a differential comparator 404 whose output is coupled to the S100 computer bus 406 via tri-state logic bus driver 408.

The decoding network 402 allows the microcomputer 344 to energize a single element among the collection of optical switches. The energized element will generate a signal which reflects the presence or absence of the movable X axis assembly at the selected position. The signal is conditioned by the differential comparator 404 and subsequently returned to the microcomputer 344 via the tri-state bus driver 408.

Figure 15:
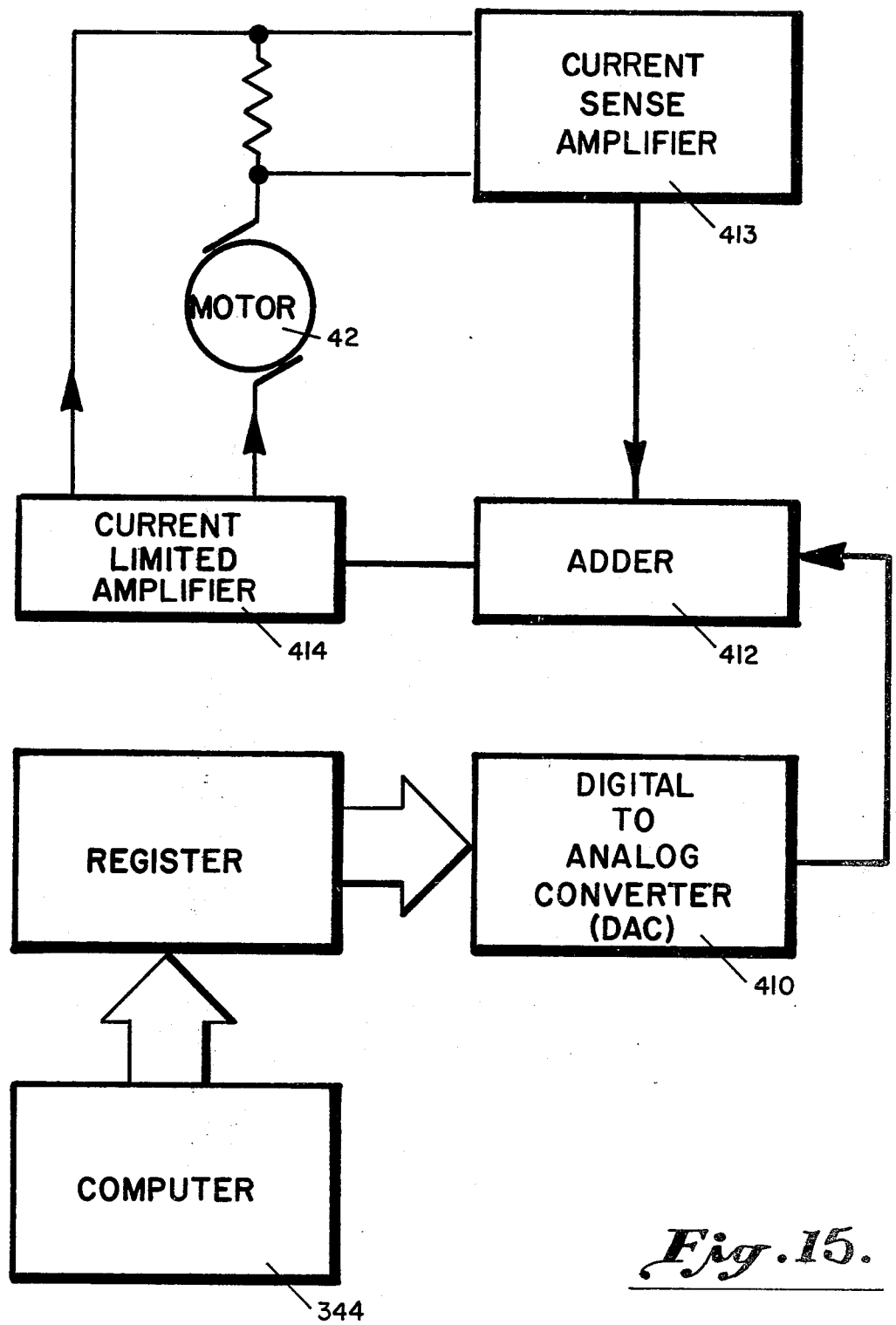
FIG. 15 is a schematic diagram of the X and Y axis motor drive circuitry.

The X and Y axis motor drive circuitry, schematically shown in FIG. 15, consists of a Digital to Analog Converter 410, a current amplifier 412, a current sensing amplifier 413, a current limiter 414, and a DC motor such as the X axis drive motor 42.

The strategem for using converters 410 is to allow for a controlled acceleration and deceleration in order to speed long-range movements without inducing jarring stops.

The converter 410 is a standard product by Analog Devices, the AD561. It is implemented by an appropriate power supply for bipolar voltage output over the range ± 5 volts. A current sensing amplifier 413 provides additional drive voltage when the motor is under load, to compensate for resistive voltage loss in the motor. The adder 412, adds the output of the current sensing amplifier to that of the digital to analog converter 410. The affect of the current sensing amplifier is to make the motor speed more nearly independent of varying load conditions, so that the carriage may move slowly and precisely without danger of stalling when lint on the tracks or a tangled line causes an extra load on the motor. The current limiting amplifier 414 boosts the power of the adder 419 and limits the current to ±

375 ma. The DC motors are standard products of Portescap, Inc. (Swiss) part #16Ml1-210.

The preferred components of the breaking circuitry are a computer-controlled current switch, the brake solenoid (e.g. solenoid 108), preferably a Dormeyer P2-1L, and mechanical flags detentents. As has been described, the solenoid and blade ride on the moving assembly. When the solenoid is de-energized, the blades drop into notches on a stationary track, locking the movable assembly in place. The IEEE standard 488 communications bus interface circuitry allows the microcomputer 344 to communicate with any instrument having a communications bus which fulfills the specifications of IEEE Standard 488. The PASS interface need implement only a few of the several IEEE 488 functions. As such, it can be selected to "talk", "listen", and can be triggered. The trigger function resets the microcomputer.

The PASS controller accepts three types of commands from the master controller 344 or computer 340 via the IEEE 488 communications bus. These commands are:
1. X axis position request;
2. Y axis position request;
3. Function request.

Furthermore, as has been noted, the PASS can indicate its operational status for interrogations by the master controller via the 488 communications bus. During the execution of the various functions, corresponding status codes will be presented to the communications bus. In this manner, the system maintains proper sequential operation of all components.

As has been noted, this invention relates to a programmable action sampler system. While it is preferred to use that sampler system as a component of a bacterial sample analyzer, as has been described, obviously the system has many uses other than just this. Indeed, it finds significant applications independent of the components schematically illustrated in FIGS. 12 and 13. All that it requires for actuation are appropriate signals supplied to its various motors, samples through its various input lines, and a vacuum source applied to its various waste and sample output lines. Supplying such information, samples and negative pressures is well within the ability of one skilled in this art. Accordingly, while a preferred embodiment of the invention has been described, variations, improvements, and modifications will be apparent to those skilled in this art. For this reason, the scope of the invention now will be defined by the following claims:

We claim the right to exclude others from making, using, or selling the following structures:

1. A programmable action sampler system for dispensing liquid samples flowing in sequence through a liquid sample line to one of a series of sample cups and for selectively addressing a sample within a sample cup, the system including
a structure adapted to receive a matrix of sample cups in predetermined locations, the openings of the sample cups generally lying in the same horizontal plane,
a waste liquid line,
a sample head including means for receiving and either dispensing liquid samples into the sample cups or for shunting liquid samples to the waste line, the sample head further including cannula means for selectively addressing or withdrawing a liquid sample in any sample cup,
a Y-axis carriage movable in a first direction over the structure matrix of receiving the sample cups,
means mounting the sample head on the Y-axis carriage for movement in a second direction relative to the structure receiving the matrix of sample cups, the first and second directions being generally orthogonal and in line with the rows and columns of the sample cup matrix structure, and
means to locate the sample head in a first and second direction relative to the structure receiving the matrix of sample cups to position the sample dispenser and the cannula means over any given sample cup and to permit the sample head to be relocated from any sample cup position to any other sample cup position, said means including element pairs, an element pair being located in line with each row and column of sample cup positions, and means to actuate the element pair associated with the row and column at which the sample head is located, the actuated pair locating the sample head relative to the sample cup matrix structure.

2. A programmable action sampler system as set forth in claim 1 including means to bathe the sample-withdrawing structure of the cannula means in a wash solution between sample addressing operations.

3. A programmable action sampler system as set forth in claim 2 in which the means for bathing the sample-withdrawing structure substantially continuously bathes the structure between sample addressing operations.

4. A programmable action sampler system as set forth in claim 1 in which the means to locate the sample head relative to the sample cups includes blade brake means associated with both the Y-axis carriage and the sample head mounting means, the blade brake means co-operating with castellated bars mounted on adjacent structure of the system, the blade brakes when actuated being received within a selected notch of each castellated bar to accurately locate and hold the sample head over a selected sample cup position in the matrix.

5. A programmable action sampler system as set forth in claim 1 including means to maintain the environment about the sample cup locations at a constant temperature.

6. A programmable action sampler system as set forth in claim 5 in which the constant temperature means includes a source of constant temperature liquid, the structure receiving the sample cups including sample cup racks, a tray receiving the sample cup racks, the tray including inlet manifold means to supply a constant flow of the constant temperature liquid from the source to the tray, and outlet manifold means to withdraw a flow of constant temperature liquid from the tray, and means to maintain a substantially uniform level of liquid within the tray, the level being beneath the level of the top of the sample cups within the rack.

7. A programmable action sampler system as set forth in claim 1 in which the cannula means includes a sensing probe for measuring a physical characteristic of the sample within any given sample cup.

8. A programmable action sampler system as set forth in claim 1 in which the cannula means includes means for withdrawing a selected sample in a sample cup and supplying the withdrawn sample to a liquid sample line.

9. A programmable action sampler system as set forth in claim 1 in which the element pairs are optical elements, one element emitting a light beam to strike a light-sensitive portion of the associated element of the pair, the actuating means including a flag structure to break the light beam of the pair associated with the sample head location.

10. A programmable action sampler system as set forth in claim 1 in which the locating means includes motors to drive the sample head relative to the Y-axis carriage, and the Y-axis carriage relative to the sample cup matrix structure, and means controlling the speed and rotational direction of the drive motors, their speed and direction determining the speed and direction of movement of the sample head, the controlling members causing the motors to move the sample head at a first speed between locations and then at a second, slower speed as the selected sample cup location is approached.

11. A programmable action sampler system as set forth in claim 10 in which the means to locate the sample head relative to the sample cups further includes blade brake means associated cups includes blade brake means associated with both the Y-axis carriage and the sample head mounting means, the blade brake means co-operating with castellated bars mounted on adjacent structure of the system, the blade brakes when actuated being received within a selected notch of each castellated bar to accurately locate and hold the sample head over a selected sample cup position in the matrix.

12. A programmable action sampler system as set forth in claim 11 in which the motor controlling means, after the blade brake means are actuated, moves the sample head in a reverse direction relative to the direction in which the head approached the selected sample cup location, to seat the blade brake means squarely in a selected notch.

13. A programmable action sampler system as set forth in claim 1 in which the means for shunting liquid samples to the waste line includes a waste chamber, the waste line being connected at the lower portion of the wash chamber, a selectively actuatable vacuum source connected to the waste line for selectively applying a vacuum to the waste chamber when samples are to be shunted to the waste line, and liquid sample lines connected to the upper portion of the waste chamber to supply the liquid samples as desired to the waste chamber, the vacuum source when applied to the waste line causing liquid samples to be shunted through the waste chamber to the waste line.

14. A programmable action sampler system as set forth in claim 13 in which the liquid sample lines terminate in the waste chamber above and substantially equally spaced from the inlet to the waste line.

15. A programmable action sampler system as set forth in claim 1 in which the structure receiving the sample cups includes sample cup racks, a tray receiving the sample cup racks, the tray including inlet manifold means to supply a constant flow of the constant temperature liquid from the source to the tray, and outlet manifold means to withdraw a flow of constant temperature liquid from the tray, and means to maintain a substantially uniform level of liquid within the tray, the level being beneath the level of the top of the sample cups within the rack.

16. A programmable action sampler system as set forth in claim 15 in which the sample cup racks and sample cups are molded as a unitary structure.

17. A programmable action sampler system as set forth in claim 1 in which the sample head includes at least one drip tube adapted to be converted to a liquid sample line, an open end of the drip tube being positionable over the matrix of sample cups, the liquid samples then being permitted to drip from the end of the drip tube into a selected sample cup location, and at least one vacuum tube with an open end adjacent the open end of the drip tube, means to selectively apply a vacuum to the vacuum tube to cause liquid samples in the drip tube to be cycled from its open end into the adjacent open end of the vacuum tube, means connecting the vacuum tube to the waste line, the end portion of the drip tube and vacuum tube adjacent the open ends being coated with a hydrophobic substance.

18. A programmable action sampler system as set forth in claim 1 including drive means to move the carriage, drive means to move the sample head, and drive means to move the cannula means, at least one of the drive means consisting of a driven member with a driven portion of semi-circular cross section, a drive member shaft having an hourglass-shaped reduced area of opposed semi-circular shape in cross section, the radius of the semi-circular drive and driven member areas being substantially the same, means holding the drive and driven members with their semi-circular areas in compressive contact, and means for selectively driving the drive member whereby rotation of the drive member causes the driven members to rotate.

* * * * *